US00PP30092P3

(12) United States Plant Patent
Mueller

(10) Patent No.: US PP30,092 P3
(45) Date of Patent: Jan. 15, 2019

(54) ***VINCA* PLANT NAMED 'RAINER'**

(50) Latin Name: *Vinca minor*
Varietal Denomination: Rainer

(71) Applicant: Hans Mueller, Kornwestheim (DE)

(72) Inventor: Hans Mueller, Kornwestheim (DE)

( * ) Notice: Subject to any disclaimer, the term of this patent is extended or adjusted under 35 U.S.C. 154(b) by 0 days.

(21) Appl. No.: 15/731,246

(22) Filed: May 11, 2017

(65) Prior Publication Data

US 2018/0332754 P1 Nov. 15, 2018

(51) Int. Cl.
*A01H 5/02* (2018.01)
*A01H 6/08* (2018.01)

(52) U.S. Cl.
USPC ..... Plt./226
CPC ..... *A01H 6/08* (2018.05)

(58) Field of Classification Search
USPC ..... Plt./263.1, 226
See application file for complete search history.

*Primary Examiner* — Susan McCormick Ewoldt

(57) ABSTRACT

A new cultivar of *Vinca* plant named 'Rainer' that is characterized by young leaves that are variegated yellow-green in color, a compact habit and violet-blue colored flowers.

2 Drawing Sheets

Botanical classification: *Vinca minor.*
Variety denomination: 'Rainer'.

BACKGROUND OF THE INVENTION

The present invention relates to a new and distinct cultivar of *Vinca* plant botanically known as *Vinca minor* and hereinafter referred to by the cultivar name 'Rainer'.

'Rainer' is a naturally occurring whole plant mutation. The new *Vinca* plant was discovered and selected by the Inventor as a single plant within a population of unnamed *Vinca minor* plants in a cultivated area of Kornwestheim, Germany in 2015.

Asexual reproduction by softwood cuttings of the new cultivar 'Rainer' was first performed in 2015 in Kornwestheim, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Vinca* cultivar 'Rainer'. These traits in combination distinguish 'Rainer' as a new and distinct cultivar apart from all other existing varieties of *Vinca* known to the inventor.

1. *Vinca* 'Rainer' exhibits young leaves that are variegated yellow-green in color.
2. *Vinca* 'Rainer' exhibits a compact habit.
3. *Vinca* 'Rainer' exhibits violet-blue flowers.

The closest comparison cultivars are *Vinca* 'Bowles Variety' (not patented) and *Vinca* 'Marie' (not patented). 'Rainer' is different than 'Bowles Variety' in the following characteristics:

1. *Vinca* 'Rainer' exhibits young leaves that are variegated yellow-green in color. In contrast, the young leaves of 'Bowles Variety' are entirely green.
2. *Vinca* 'Rainer' exhibits a compact habit. In contrast, 'Bowles Variety' has a more open habit.

'Rainer' is different than 'Marie' in the following characteristics:

1. *Vinca* 'Rainer' exhibits young leaves that are variegated yellow-green in color. In contrast, the young leaves of 'Marie' are entirely green.
2. *Vinca* 'Rainer' exhibits flowers that are larger in diameter than the flowers of 'Marie'.

In comparison to the parent plant of the *Vinca minor* species, 'Rainer' is different in the following characteristics:

1. *Vinca* 'Rainer' exhibits young leaves that are variegated yellow-green in color. In contrast, young leaves of plants of the *Vinca minor* species are entirely green.
2. *Vinca* 'Rainer' exhibits flowers that are larger in diameter than the flowers of plants of the *Vinca minor* species.

BRIEF DESCRIPTION OF THE DRAWING

The accompanying photographs illustrates the distinguishing traits of *Vinca* 'Rainer'.

The plant in the photograph of sheet 1 shows an overall view of a 12 month old plant.

Sheet 2 is a close-up photograph of the young foliage and flowers.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Vinca* cultivar named 'Rainer'. Data was collected in Kornwestheim, Germany from 12 month old outdoor grown plants in 9 cm. diameter containers. The time of year was Spring and the temperature averaged 20° Centigrade during the day and 10° Centigrade at night. The light level was natural outdoor light. Color determinations are in accordance with The Royal Horticultural Society Colour Chart 2015 edition, except where general color terms of ordinary dictionary significance are used. The growing requirements are similar to the species.

'Rainer' has not been tested under all possible conditions and phenotypic differences may be observed with variations in environmental, climatic, and cultural conditions, however, without any variance in genotype.

Botanical classification: *Vinca minor* 'Rainer'.

Plant type: Perennial groundcover or sub-shrub.

Parentage: 'Rainer' was discovered as a naturally occurring whole plant mutation in a population of unnamed *Vinca minor* plants.

Vigor: Moderate.

Growth habit: Young plants are broad spreading to upright, mature plants are creeping.

Plant shape: Young plants are broad rounded to upright, mature plants are procumbent.

Suitable container size: 9 cm. containers and larger.

Overall plant height: Average 13.4 cm.

Overall plant width: Average 15.6 cm.

Low temperature tolerance: −25 degrees Centigrade.

High temperature tolerance: 35 degrees Centigrade.

Propagation: Softwood cuttings.

Time to initiate roots (summer): Approximately 50 days to produce roots on an initial cutting at 20 degrees Centigrade.

Time to initiate roots (winter): Approximately 70 days to produce roots on an initial cutting at 4 degrees Centigrade.

Time to produce a rooted cutting or liner (summer): Approximately 90 days at 20 degrees Centigrade.

Time to produce a rooted cutting or liner (winter): Approximately 150 days at 20 degrees Centigrade.

Crop time: From a rooted cutting, approximately 52 weeks are required to produce a finished plant.

Root system: Fine and fibrous.

Stem:

- *Branching habit*.—Freely branching from base.
- *Average number of lateral branches*.—28.
- *Pinching*.—No.
- *Lateral branch diameter*.—Average 1.5 mm. in diameter.
- *Lateral branch length*.—Average 11.7 cm. in length.
- *Internode length*.—Average 1.4 cm. between nodes.
- *Shape*.—Round in cross-section.
- *Lateral branch angle*.—35 degrees from vertical.
- *Strength*.—Strong.
- *Texture*.—Smooth.
- *Pubescence*.—Absent.
- *Luster*.—Moderately glossy.
- *Young stem color*.—144A.
- *Mature stem color*.—138B.
- *Stem color at internodes*.—138B.

Foliage:

- *Leaf arrangement*.—Opposite.
- *Compound or single*.—Single.
- *Quantity of leaves per lateral branch*.—Average 12.
- *Leaf length*.—Average 2.7 cm. in length.
- *Leaf width*.—2.0 cm. in width.
- *Leaf shape*.—Ovate to broad elliptic.
- *Leaf apex*.—Bluntly acute.
- *Leaf base*.—Acute.
- *Leaf lobes*.—Not lobed.
- *Leaf texture*.—Smooth both sides.
- *Leaf pubescence*.—Absent both sides.
- *Leaf luster*.—Glossy both sides.
- *Leaf margin*.—Entire.
- *Vein pattern*.—Pinnate.
- *Young leaf color* (*lower surface*).—137C and 144A to 144B.
- *Young leaf color* (*upper surface*).—137A and 144B to 144C.
- *Mature leaf color* (*lower surface*).—146B.
- *Mature leaf color* (*upper surface*).—Between NN137A and 147A.
- *Vein color* (*lower surface*).—145A.
- *Vein color* (*upper surface*).—144B.
- *Leaf attachment*.—Petiolate.
- *Petiole dimensions*.—Average 7.0 mm. in length and 1.2 mm. in width.
- *Petiole texture*.—Smooth.
- *Petiole luster*.—Moderately glossy.
- *Petiole strength*.—Medium strong.
- *Petiole color*.—Upper side 146B, lower side 146C.

Flower:

- *Flower arrangement*.—Single salverform flowers emerge from axillary nodes.
- *Quantity of flowers per plant*.—Average 10.
- *Quantity of flower buds per plant*.—Average 18.
- *Quantity of flowers and buds per plant*.—Average 28.
- *Flowering season*.—March and April.
- *Fragrance*.—Absent.
- *Flower shape*.—Salverform.
- *Flower bud length*.—Average 1.9 cm. in length.
- *Flower bud diameter*.—Average 0.4 cm. in diameter.
- *Flower bud shape*.—Narrow elliptic.
- *Flower bud texture*.—Smooth.
- *Flower bud luster*.—Moderately glossy.
- *Flower bud color*.—Between 92D and 115D, towards base 138C to 138D, immature calyx between 143C and 144A.
- *Flower aspect*.—Outward.
- *Flower dimensions*.—Average 3.7 cm. in diameter and 1.9 cm. in height.
- *Flower tube length*.—Average 1.3 cm.
- *Flower tube diameter*.—Distal end 0.7 cm, proximal end 0.3 cm.
- *Flower longevity*.—Average 10 days.
- *Petal number*.—5.
- *Petal fused or unfused*.—Lower 30% fused.
- *Petal dimensions*.—Average 2.5 cm. in length and 2.8 cm. in width.
- *Petal shape*.—Spathulate.
- *Petal texture*.—Smooth both sides, slightly velvety.
- *Petal luster*.—Matte both sides.
- *Petal margin*.—Entire, slightly undulate.
- *Petal rugose*.—Both sides non-rugose.
- *Petal apex*.—Broad bluntly acute.
- *Petal base*.—Fused into tube.
- *Petal color when opening* (*upper side*).—Between N88B and N89D.
- *Petal color when opening* (*under side*).—92A, toward base 92C.
- *Petal color fully open* (*upper side*).—N88B.
- *Petal color fully open* (*under side*).—Between 90D and 92A.
- *Petal color fading to*.—Not fading.
- *Self-cleaning or persistent*.—Self-cleaning.

Calyx:

*Calyx shape*.—Rotate.

*Calyx dimensions*.—7.0 mm. in length and 3.5 mm. in diameter.

Sepals:

*Sepal arrangement*.—Rotate.

*Number of sepals*.—5.

*Sepal shape*.—Lanceolate.

*Sepal margin*.—Entire.

*Sepal apex*.—Acute.

*Sepal base*.—Broad cuneate.

*Sepals fused*.—Not fused.

*Sepal texture*.—Smooth both sides.

*Sepal luster*.—Slightly glossy both sides.

*Sepal dimensions*.—4.0 mm. in length and 1.2 mm. in width.

*Sepal color when opening* (*upper side*).—143A.

*Sepal color when opening* (*under side*).—143B.

*Sepal color fully opened* (*upper side*).—143B.

*Sepal color fully opened* (*under side*).—143C.

Pedicels:

*Pedicel dimensions*.—Average 2.0 cm. in length and 1.0 mm. in diameter.

*Pedicel angle*.—25° from vertical.

*Pedicel color*.—143B to 143C.

*Pedicel strength*.—Moderately strong.

Reproduction organs:

*Stamen number*.—5.

*Filament length*.—2.0 cm.

*Filament color*.—145B.

*Anther shape*.—Basifixed, elliptic, tips touching forming a small cone.

*Anther dimensions*.—2.5 mm. in length and 1.0 mm. in width.

*Anther color*.—152C.

*Amount of pollen*.—Moderate.

*Pollen color*.—156D.

*Pistil number*.—One.

*Pistil length*.—Average 7.0 mm.

*Stigma diameter*.—Average 2.0 mm.

*Stigma shape*.—Club shaped.

*Stigma color*.—NN155D.

*Style length*.—Average 5.0 mm.

*Style color*.—145C.

*Ovary color*.—144A to 144B.

Fruit and seed: 'Rainer' has not produced fruit or seed to date.

Disease and pest resistance: Disease and pest resistance has not been observed to date.

The invention claimed is:

1. A new and distinct variety of *Vinca* plant named 'Rainer' as described and illustrated.

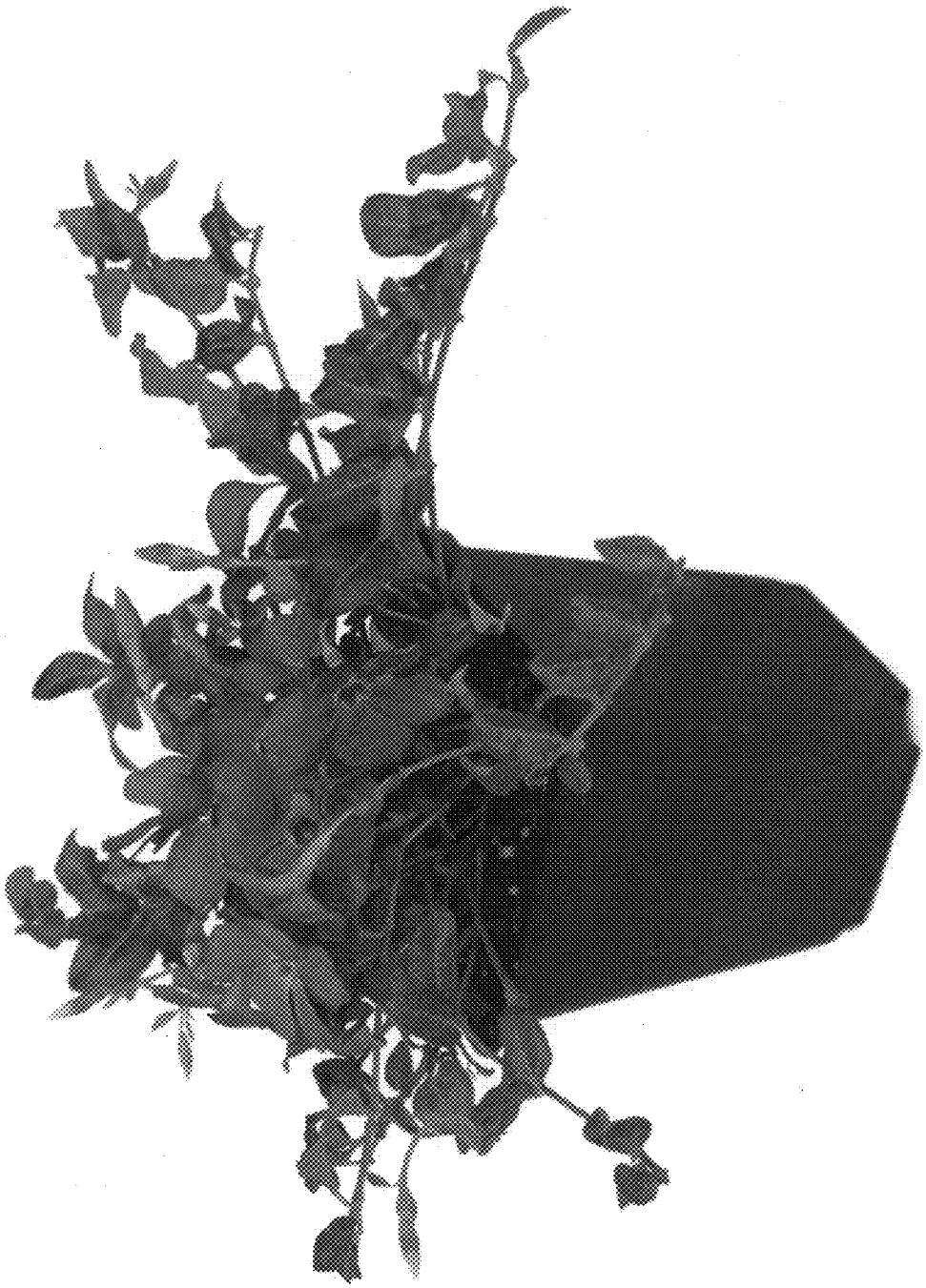

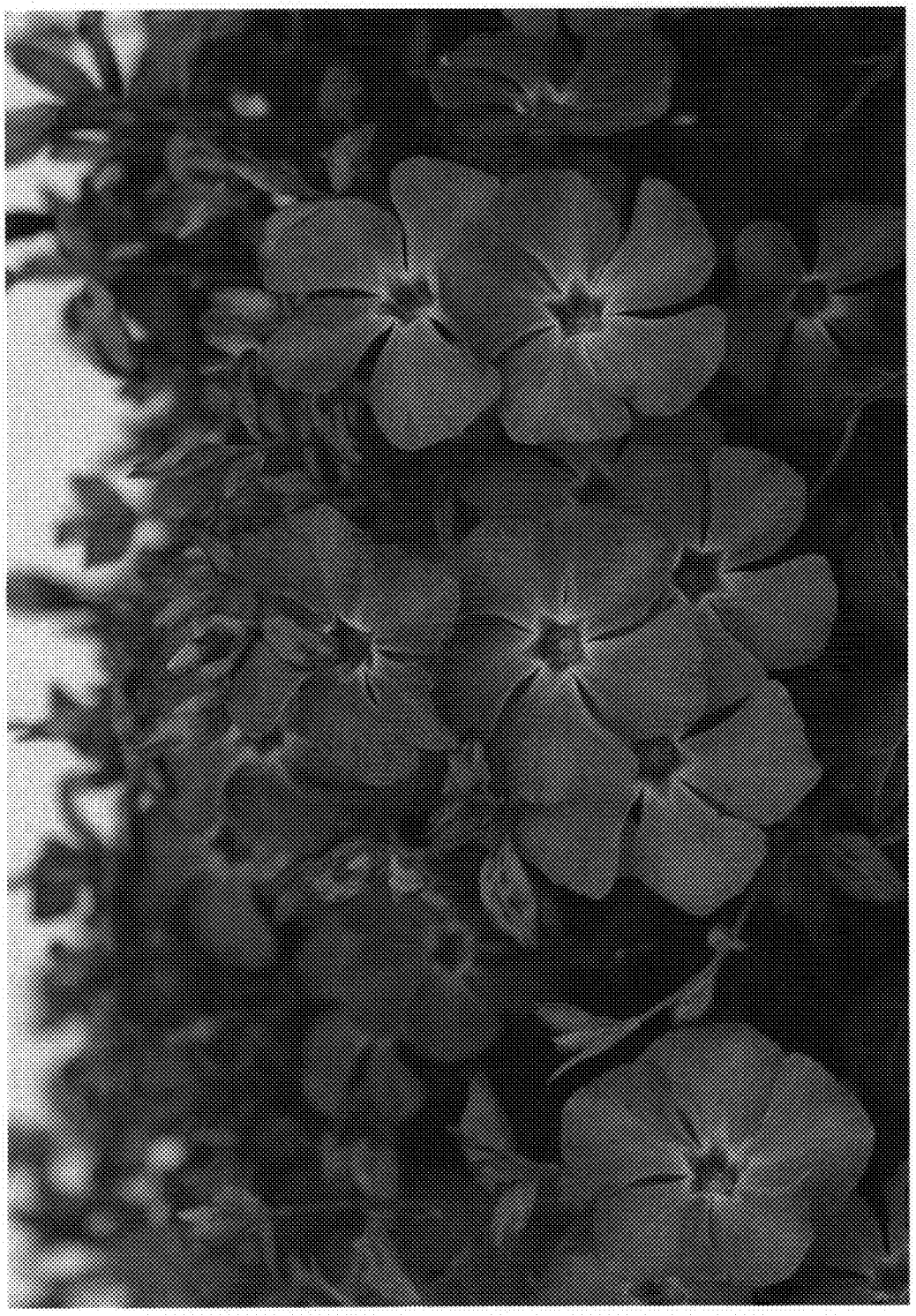

* * * * *